United States Patent [19]
Fändriks et al.

[11] Patent Number: 6,096,772
[45] Date of Patent: Aug. 1, 2000

[54] USE OF ANGIOTENSIN II TYPE 1 RECEPTOR ANTAGONISTS IN THE TREATMENT OF DYSPEPTIC SYMPTOMS

[75] Inventors: Lars Fändriks, Askim; Anders Pettersson, Kode, both of Sweden

[73] Assignee: Astra Aktiebolag, Sodertalje, Sweden

[21] Appl. No.: 08/702,522

[22] PCT Filed: Jun. 10, 1996

[86] PCT No.: PCT/SE96/00758

§ 371 Date: Aug. 28, 1996

§ 102(e) Date: Aug. 28, 1996

[87] PCT Pub. No.: WO97/00070

PCT Pub. Date: Jan. 3, 1997

[30] Foreign Application Priority Data

Jun. 19, 1995 [SE] Sweden .................................. 9502219

[51] Int. Cl.[7] ...................... A61K 31/41; A61K 31/4709; A61K 31/506; A61K 31/519

[52] U.S. Cl. .......................... 514/381; 514/258; 514/275; 514/312

[58] Field of Search .................................. 514/381, 312, 514/303, 275, 258

[56] References Cited

U.S. PATENT DOCUMENTS

| | | | |
|---|---|---|---|
| 5,155,118 | 10/1992 | Carini et al. | 514/381 |
| 5,212,195 | 5/1993 | Clark | 514/381 |
| 5,538,991 | 7/1996 | Ashton et al. | 514/397 |

FOREIGN PATENT DOCUMENTS

| | | |
|---|---|---|
| 0253310 | 1/1988 | European Pat. Off. . |
| 0459136 | 12/1991 | European Pat. Off. . |
| 0555825 | 8/1993 | European Pat. Off. . |
| 2263635 | 8/1993 | United Kingdom . |
| 2263636 | 8/1993 | United Kingdom . |
| 2263637 | 8/1993 | United Kingdom . |
| 2263638 | 8/1993 | United Kingdom . |
| 2263639 | 8/1993 | United Kingdom . |

OTHER PUBLICATIONS

Byyny R.L.: "Losartan potassium lowers blood pressure measured by ambulatory blood pressure monitoring", Journal of Hypertension, Supplement, (1995) 13/1 (S29–S33) (Abstract).

*Primary Examiner*—Phyllis G. Spivack
*Attorney, Agent, or Firm*—White & Case LLP

[57] ABSTRACT

A method for the prophylaxis and treatment of dyspeptic symptoms comprising administering angiotensin II type 1 receptor antagonists in pharmaceutical preparations is disclosed.

6 Claims, No Drawings

USE OF ANGIOTENSIN II TYPE 1 RECEPTOR ANTAGONISTS IN THE TREATMENT OF DYSPEPTIC SYMPTOMS

FIELD OF THE INVENTION

The present invention is related to the use of angiotensin II type 1 receptor antagonists for the prophylaxis and/or treatment of dyspeptic symptoms and to the manufacture of pharmaceutical preparations with effects on dyspeptic symptoms.

BACKGROUND ON THE INVENTION

Angiotensin II type 1 receptor antagonists for which the present invention has found a new medical use are known in the art. However, nothing has been reported or is generally known concerning the pharmacological and/or therapeutic properties of these compounds with respect to effects on dyspeptic symptoms.

In connection with the present invention an angiotensin II type 1 receptor antagonist of the general formula I is employed:

I wherein A is

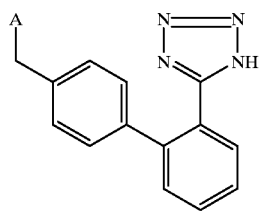

I:1

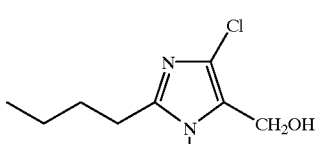

I:2

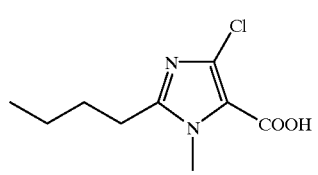

I:3

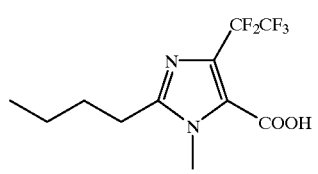

I:4

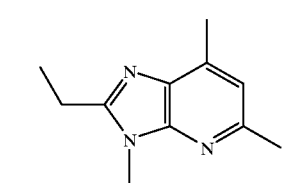

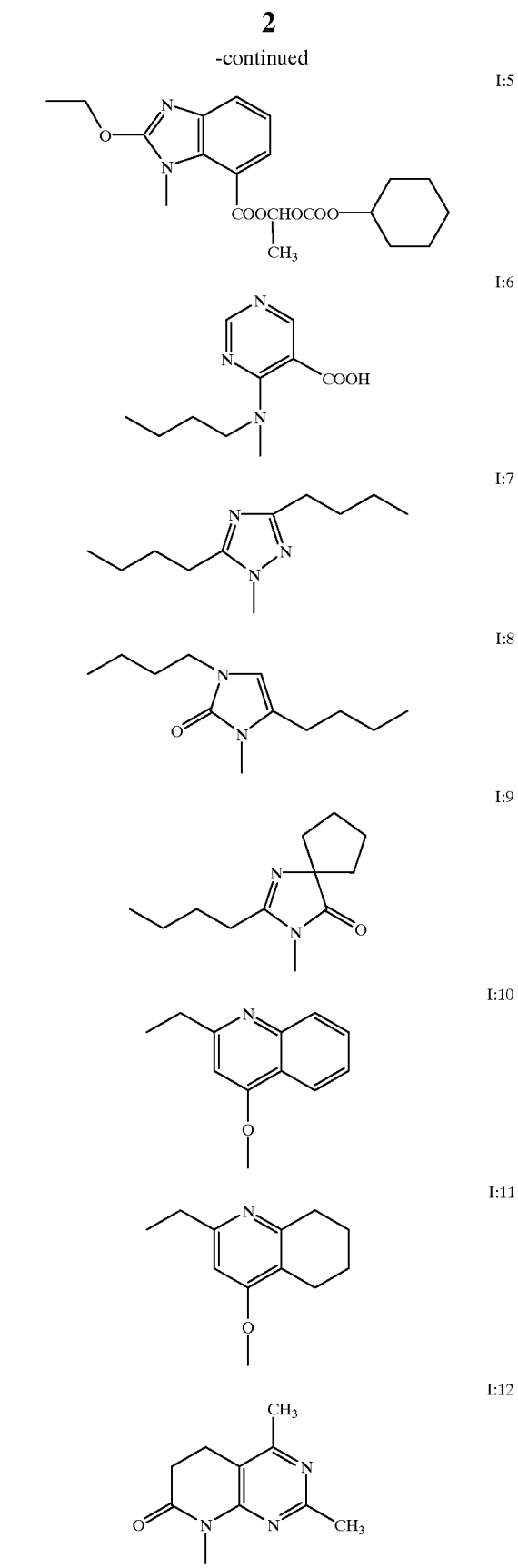

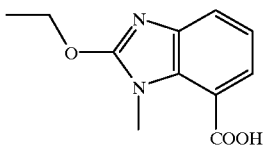

I:13

The compounds listed above may be used in racemic form or in the form of a substantially pure enantiomer; they may be used in neutral form or in the form of a salt, preferably a physiologically acceptable salt such as sodium, potassium, ammonium, calcium or magnesium. Where applicable the compounds listed above can be used in hydrolysable ester form.

The compound of the formula I wherein A is the I:1 moiety has the generic name losartan and is known from European patent no. 253 310.

The compound of the formula I wherein A is the I:5 moiety has the generic name candesartan cilexetil, code no. TCV-116 and is known from EP-459 136.

The compound of the formula I wherein A is the I:9 moiety is known under the generic name irbesartan.

The compound of the formula I wherein A is the I:13 moiety has the generic name candesartan and is known from EP-459 136.

Functional disorders of the gastrointestinal tract are common and account for a very large number of medical consultations. On an annual basis approximately 30% of the western population experience such dyspeptic symptoms varying from mild indigestion to severe pain. The symptomatology may be due to an organic disease (for example peptic ulcer disease) or, more commonly, be without any known origin (i.e. absence of organic pathology in the upper gut as evidenced by various diagnostic procedures). In clinical routine the latter symptom-syndrome is commonly called "non-ulcer dyspepsia", "functional dyspepsia", "non organic dyspepsia" etc. Treatment of dyspepsia of unknown origin involves a variety of pharmacological principles (i.e. neutralization of gastric acidity, drugs affecting the motility of the gut wall etc.) some of which have doubtful efficacy and sometimes with severe side effects.

Dyspepsia due to peptic ulcers can be cured by intake of antacids and inhibitors of gastric acid secretion. Ulcer-like dyspeptic symptoms without mucosal pathology are usually also sensitive to a similar treatment. This subpopulation of dyspeptic symptoms (acid related dyspepsia) is thus defined by the symptom-relief in association with intake of neutralizing agents or inhibition of gastric acid production by use of proton pump inhibitors or histamine type2-receptor antagonists. However the former principle is shortlasting and neutralizing drugs must thus be administered repeatedly during the day. The latter drugs have disadvantages of being expensive and exert a great impact on gut physiology as the antacid gastric conditions increase the risk for intestinal and/or systemic infections. Prokinetic drugs (such as cisapride) or anticholinergic compounds are other pharmaceutical principles that are utilize for dyspeptic symptoms, usually with variable effect and high frequency of side effects. It follows that available drug regimens for treating dyspeptic symptoms are impaired by serious disadvantages.

Compounds that interfere with the renin-angiotensin system (RAS) are well-known in the art and are used to treat cardiovascular diseases, particularly arterial hypertension and cardiac failure. Principally, the RAS can be interfered with by inhibition of the enzymes synthesizing angiotensins or by blocking receptors at the effector sites. Available today are renin-antagonists, inhibitors of the angiotensin converting enzyme (ACE) and angiotensinII-receptor (AII-receptor) antagonists. In addition to cardiovascular effects, some of these compounds have been claimed to exert effects on unspecified "gastrointestinal disorders".

DISCLOSURE OF THE INVENTION

The exact mechanisms behind acid related complaints form the upper gastrointestinal tract are today unknown. A prerequisite is however that luminal acid get access to the superficial mucosal cells. This is not the case during normal conditions, as a continuous transport of fluid and bicarbonate provides a neutral compartment at the mucosal surface. This important acid neutralizing process is governed by a complex network of different regulatory mechanisms.

The invention describes a new method to treat dyspeptic symptoms by modulating the gastroduodenal mucosal surface-neutralizing capacity, by pharmacological interference with RAS.

Renin-angiotensin system (RAS):

It is known that RAS, in concert with the sympathetic nervous system decreases the gastroduodenal acid neutralizing capacity. As above, several different methods can be used in order to interfere with RAS.

It has now surprisingly been found that pharmacological blockade of specific AII type 1 receptors with angiotensin II type receptor antagonists, reverses the inhibitory effects of AII to enhancement of gastroduodenal acid neutralizing capacity. Thus, elevated plasma AII concentrations in the presence of angiotensin II type 1 receptor blockade strengthens surface neutralizing capacity, in turn eliminating one prerequisite for the induction of symptoms by luminal acid.

The present application discloses that administration of specific AII type 1 receptor blockers, via an improved gastroduodenal mucosal acid neutralizing capacity, dyspeptic symptoms.

The present invention thus relates to a new method of treating dyspepsia by pharmacological interference with the renin-angiotensin system using known compounds of the general formula I above.

Thus, it has now unexpectedly been found that compounds of the general formula I

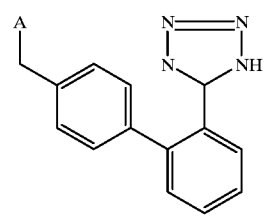

I wherein A is

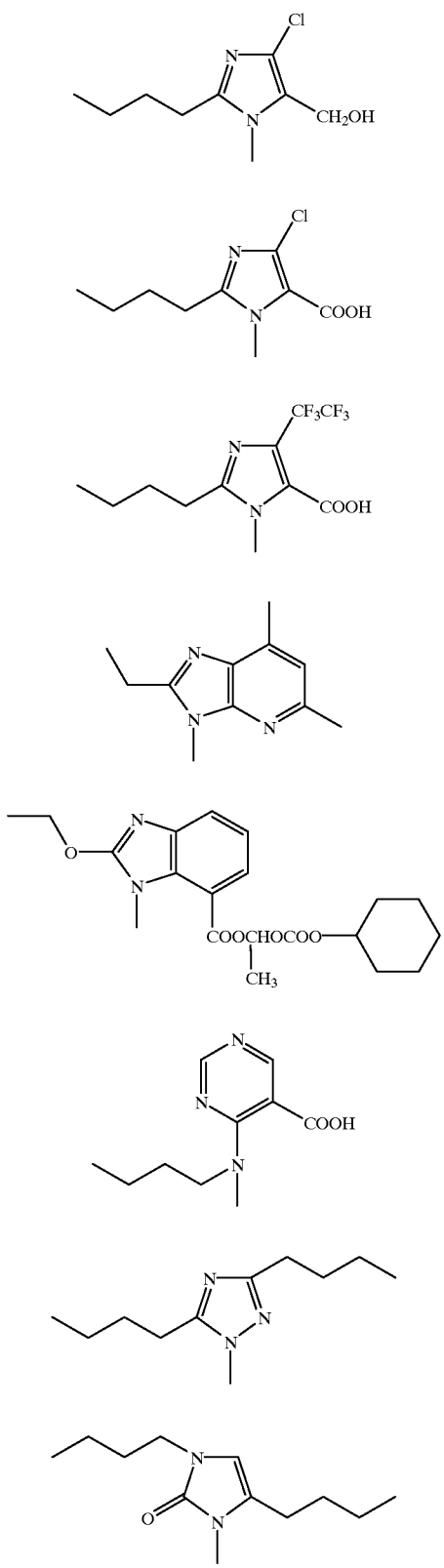

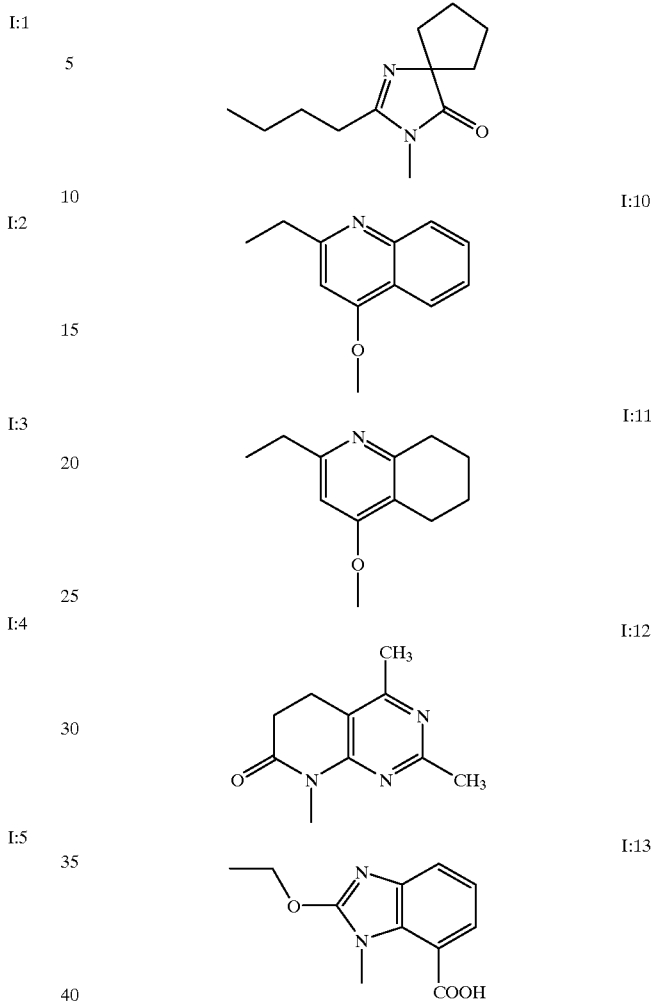

or a physiologically acceptable salt and/or a stereochemical isomer thereof are effective in the prophylaxis and/or treatment of dyspeptic symptoms.

While the effects on gastroduodenal acid neutralizing capacity have been established in animals by the intravenous route, it is believed that the effect is a systemic effect which is not dependent on the mode of administration that is used, and accordingly the effect will be seen also with other routes of administration such as rectal or oral administration.

The dose of a compound according to formula I to be administered for prophylaxis and/or treatment of dyspeptic symptoms will vary depending on factors such as the severity of the disease and the status of the patient. The dosage range at oral, rectal as well as intravenous administration will be in the interval from 1 to 500 mg per day.

The preferred mode of the invention is the use of a compound of the formula I wherein A is I:1 (Losartan) or I:5 (T CV-116).

Scientific tests

In order to study the gastroduodenal acid neutralizing capacity, the following experiments were performed in anesthetized rats. Intravenous administration of AII in the untreated animals was followed by a slightly decreased ability to neutralize acid. In animals pretreated with the AII-receptor blocker Losaran, an enhanced acid neutralizing capacity was found in response to the same dose of AII.

TABLE 1

Duodenal mucosal acid-neutralizing capacity in anesthetized rats before and during intravenous administration of AII.

|  | Untreated animals ($\mu$Eq/h × cm) | Losartan-treated animals ($\mu$Eq/h × cm) |
| --- | --- | --- |
| Baseline | 12 ± 1.5 | 13 ± 1.2 |
| During AII-infusion | 10 ± 3 | 22 ± 2.3* |

Data are given as means ±SEM, n=6+6. Significant intergroup difference (students t-test, unpaired samples) is indicated by an asterisk. Intravenous administration of AII results in an impaired acid neutralizing capacity in untreated animals. In animals which are pretreated with the angiotensin II receptor blocking agent losaran, the same dosage of a AII significantly increases the acid neutralizing capacity of the duodenal mucosa.

Pharmaceutical preparations

Conventional pharmaceutical preparations can be used. The pharmaceutical preparations are preferably in the form of injection solutions, but it is also possible to use other kinds of preparations, such as oral solutions, or suspensions, tablets or capsules. Alternative routes of administration are sublingual tablets or solutions and rectal solutions, suspensions or rectiols.

The pharmaceutical preparation contains between 1 mg and 500 mg of active substance, preferably 10 to 250 mg.

What is claimed is:

1. A method for the prophylaxis and/or treatment of dyspeptic symptoms in mammals, which comprises administering to a mammalian host in need of such prophylaxis and/or treatment an effective amount of a compound of formula I

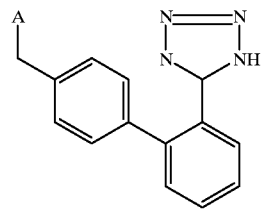

I or a physiologically acceptable salt, hydrolyzable ester and/or stereochemical isomer thereof wherein A is selected from the group consisting of

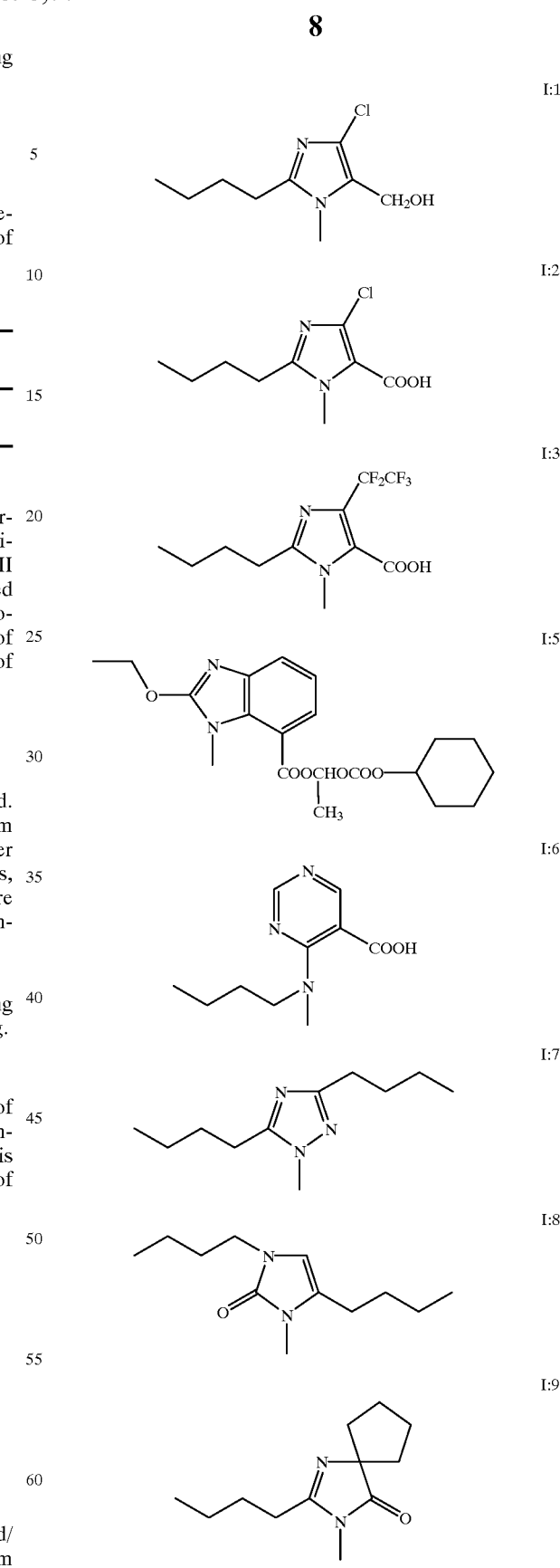

-continued

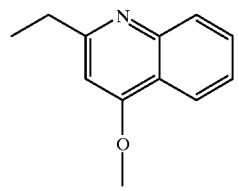
I:10

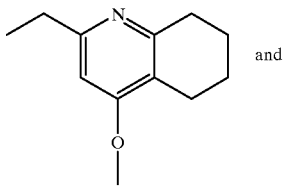
I:11

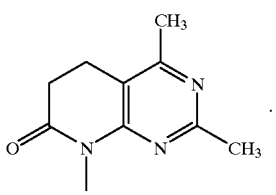
I:12

2. A method for the prophylaxis and/or treatment of dyspeptic symptoms in mammals, which comprises administering to a mammalian host in need of such prophylaxis and/or treatment an effective amount of a compound of formula I

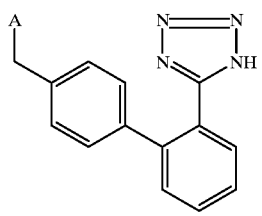
I or a physiologically acceptable salt, hydrolyzable ester and/or stereochemical isomer thereof wherein A is selected from the group consisting of

I:1

I:5 and

3. The method according to claim 2, wherein A is the I:1 moiety.

4. The method according to claim 2, wherein A is the I:5 moiety.

5. The method according to claim 1 or 2, which comprises administering the compound or salt, ester and/or stereochemical isomer thereof in association with a pharmaceutically acceptable carrier.

6. The method according to claim 1 or 2, wherein the effective amount is in the range of from 1 to 500 mg per day.

* * * * *